United States Patent
Reed

(10) Patent No.: US 11,236,176 B2
(45) Date of Patent: Feb. 1, 2022

(54) SERPINF2-BINDING MOLECULES AND METHOD OF USE THEREOF

(71) Applicant: Translational Sciences Inc., Memphis, TN (US)

(72) Inventor: Guy L. Reed, Memphis, TN (US)

(73) Assignee: Translational Sciences Inc., Memphis, TN (US)

( * ) Notice: Subject to any disclaimer, the term of this patent is extended or adjusted under 35 U.S.C. 154(b) by 443 days.

(21) Appl. No.: 14/198,804

(22) Filed: Mar. 6, 2014

(65) Prior Publication Data

US 2014/0220034 A1    Aug. 7, 2014

Related U.S. Application Data

(63) Continuation of application No. PCT/US2012/053900, filed on Sep. 6, 2012.

(60) Provisional application No. 61/531,278, filed on Sep. 6, 2011.

(51) Int. Cl.
*C07K 16/38* (2006.01)
*C07K 16/18* (2006.01)
*A61K 39/00* (2006.01)

(52) U.S. Cl.
CPC .............. *C07K 16/38* (2013.01); *C07K 16/18* (2013.01); *A61K 2039/505* (2013.01)

(58) Field of Classification Search
CPC .......................... A61K 2039/505; C07K 16/38
See application file for complete search history.

(56) References Cited

U.S. PATENT DOCUMENTS

| | | | |
|---|---|---|---|
| 6,114,506 A * | 9/2000 | Reed | A61K 39/395 424/130.1 |
| 6,411,506 B1 | 6/2002 | Hipp et al. | |
| 6,946,438 B1 * | 9/2005 | Nagai | A61K 38/484 514/15.1 |
| 7,309,774 B2 | 12/2007 | McKee et al. | |
| 2003/0031664 A1 | 2/2003 | Reed | |
| 2010/0086536 A1 | 4/2010 | Reed | |

FOREIGN PATENT DOCUMENTS

| | | | |
|---|---|---|---|
| EP | 0 272 609 A2 | 6/1988 | |
| WO | 99/61072 A2 | 12/1999 | |
| WO | 0018436 A1 | 4/2000 | |
| WO | WO 0018436 A1 * | 4/2000 | ........... A61K 38/484 |
| WO | 02072769 A2 | 9/2002 | |
| WO | 2004/042000 A2 | 5/2004 | |
| WO | 2006/005583 A2 | 1/2006 | |
| WO | 2006133403 A2 | 12/2006 | |
| WO | 2008134577 A1 | 11/2008 | |
| WO | WO 2008134577 A1 * | 11/2008 | ............... C12Q 1/56 |
| WO | 2010071787 A1 | 6/2010 | |
| WO | 2011083145 A1 | 7/2011 | |

OTHER PUBLICATIONS

Vajdos et al. Comprehensive fucntional maps of the antigen-binding site of an anti-ErbB2 antibody obtainedi with shotgun scanning mutagenesis. Journal of Molecular Biology, Jul. 5, 2002;320(2):415-28.*
Brown et al. Tolerance to single, but not multiple, amino acid replacements in antibody Vh CDR2. Journal of Immunology May 1996; 156(9):3285-91.*
McKeague et al. CHallenges and opportunities for small molecule aptamer development. Journal of Nucleic Acids, 2012; 74891.*
Nagai et al. Depletion of circulating a2-antiplasmin by intravenous plasmin or immunoneutralization reduces focal cerebral ischemic injury in the absence of arterial recanalization. Blood, 2001; 97:3086-3092.*
Wang et al. Tissue plasminogen activator increases neuronal damage after focal cerebral ischemia in wild-type and tpa deficient mice. Nature Medicine, 1998; 4(2):228-231.*
Vajdos et al. J Mol Biol. Jul. 5, 2002;320(2):415-28 at 416 (Year: 2002).*
Nagai et al. Blood, 2001; 97:3086-3092 (Year: 2001).*
Vajdos et al. J Mol Biol. Jul. 5, 2002;320(2):415-28 (Year: 2002).*
Brown et al. J Immunol. May 1996; 156(9):3285-91 (Year: 1996).*
Ferrara et al. mABs, 2015; 7(1): 32-41 (Year: 2015).*
NINDS t-PA Stroke Study. Stroke, 1997;28: 2109-2118 (Year: 1997).*
Wang et al. Nature Medicine, 1998; 4(2):228-231 (Year: 1998).*
Reed et al. PNAS, 1990; 87:1114-1118 (Year: 1990).*
Anonick et al., 1991, "Soluble Fibrin Preparations Inhibit the Reaction of Plasmin with Alpha-2-Macroglobulin: Comparison with Alpha-2-Antiplasmin and Leupeptin," Biochem. J., vol. 275, pp. 53-59.
Holmes et al., 1987, "Characterization of Recombinant Human cu2-Antiplasmin and of Mutants Obtained by Site-Directed Mutagenesis of the Reactive Site," Biochemistry, vol. 26, p. 5133.
Potempa et al., 1988, "Alpha-2-Antiplasmin: A Serpin with Two Separate but Overlapping Reactive Sites," Science, vol. 241, No. 4866, pp. 699-700 (abstract only).
International Search Report for PCT/US08/061662 (1 page) dated Aug. 18, 2008.
Sazonova et al., 2007, "Fibrinolysis is Amplified by Converting Alpha 2-Antiplasmin from a Plasmin Inhibitor to a Substrate," Journal of Thrombosis and Haemostasis, 5:2087-2094.
Hua Ya et al: "Plasminogen activator inhibitor-1 induction after experimental intracerebral hemorrhage", Journal of Cerebral Blood Flow and Metabolism, vol. 22, No. 1, Jan. 2002, pp. 55-61.

(Continued)

*Primary Examiner* — Vanessa L. Ford
*Assistant Examiner* — Sandra E Dillahunt
(74) *Attorney, Agent, or Firm* — Eversheds Sutherland (US) LLP

(57) ABSTRACT

Compositions and methods of using SerpinF2-binding molecules for preventing and/or reducing organ damage, functional disability or mortality in a patient at risk due to the activity of SerpinF2 and/or plasminogen activators on tissue injury. Also provided are compositions and methods of using SerpinF2-binding molecules for inhibiting hemorrhage, edema, and apoptosis. Methods for the preparation of medicaments for such methods of treatment and prevention are provided.

17 Claims, 8 Drawing Sheets

(56) References Cited

OTHER PUBLICATIONS

Soeda Shinji et al: "Anti-apoptotic roles of plasminogen activator inhibitor-1 as a neurotrophic factor in the central nervous system", Thrombosis and Haemostasis, vol. 100, No. 6, Dec. 2008, pp. 1014-1020.
Miura O et al: "Molecular basis for congenital deficiency of alpha 2-plasmin inhibitor. A frameshift mutation leading to elongation of the deduced amino acid sequence.", Journal of Clinical Investigation, vol. 83, No. 5, May 1, 1989, pp. 1598-1604.
European Search Report for International Application PCT/US2012/053900 dated Mar. 25, 2015.
J. C. Rau et al: "Serpins in thrombosis, hemostasis and fibrinolysis", Journal of Thrombosis and Haemostasis, vol. 5, Jul. 1, 2007 (Jul. 1, 2007), pp. 102-115.
Japanese Office Action for JP Application No. 2014-529840 dated Apr. 27, 2016 (9 pages with English translation).
"Embolectomy for Cerebral Embolism in the Acute Stage Focused on Middle Cerebral Artery Embolism," Advances in Medical Sciences, 1989, 151(1):47 (5 pages with English translation).
Maeda et al., "Brain Ischemia Model: Approach to Developing a Brain Infarction Model Using Iron Powder Particles," Therapeutic Research, 2006, 27(9):1668-1674 (20 pages with English translation).
Tanaka, "Significant of Neuroprotection," Brain Science, 1996, 7(4):389-394 (23 pages with English translation).
Canadian Examination Report for CA Application No. 2,846,667 dated Jan. 13, 2021 (5 pages).
Nagai et al., "Role of Plasminogen System Components in Focal Cerebral Ischemic Infarction, a Gene Targeting and Gene Transfer Study in Mice," Circulation, 1999, 99(18):2440-2444.

\* cited by examiner

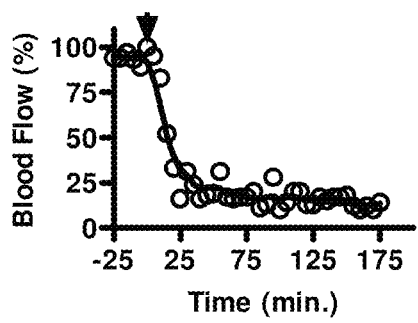 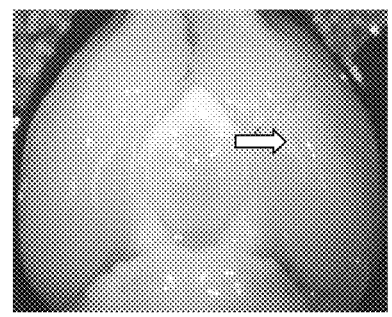
FIGURE 1A                    FIGURE 1B

SERPINF2-BINDING MOLECULES AND METHOD OF USE THEREOF

CROSS REFERENCES TO RELATED APPLICATIONS

This application is a continuation of PCT Application No. PCT/US2012/053900 filed on Sep. 6, 2012 which claims priority to U.S. Provisional Application No. 61/531,278, filed Sep. 6, 2011, the entire contents of which are incorporated by reference herewith.

ACKNOWLEDGEMENT OF FEDERAL RESEARCH SUPPORT

This invention was made, in part, with Government support under National Institute of Health Grant Nos. HL092750 & NS073147. Accordingly, the United States Government has certain rights in this invention.

FIELD OF THE INVENTION

This invention relates generally to compositions and methods for preventing or reducing morbidity, disability and death from cellular damage, hemorrhage and organ swelling after tissue injury, due to the activity of SerpinF2 in conditions typically associated with increased levels of plasminogen activators.

BACKGROUND

Tissue injury to the heart, brain, kidney and lungs may trigger the death of cells from toxicity, necrosis, apoptosis and other mechanisms. This triggers structural degradation of organ components, breakdown of vascular barriers and cellular swelling. The result may be organ edema, hemorrhage and loss of function. For example, brain edema or swelling is a feared complication of trauma, injury or stroke that can cause death or disability.[1] Brain swelling may also follow hemorrhage.[2] In the eye, macular edema may occur following central retinal vein occlusion.[3] Myocardial edema is an early marker of myocardial ischemia.[4,5] Ischemia-reperfusion increases lung permeability and induces lung edema as well.[6] Ischemia and reperfusion in one organ may cause edema in that organ and, in addition cause swelling and dysfunction in others. For example, ischemia-reperfusion of the bowel may result in edema of the bowel as well as the kidney and lung.[7] Similarly, ischemia in the liver may result in liver and kidney injury and edema.[8] Ischemia and reperfusion lead to breakdown of the vascular barrier and edema of the pancreas.[9] Ischemia and reperfusion leads to death and apoptosis of endothelial cells.[10] Microvascular injury occurs after ischemia and reperfusion.[11]

Stroke is a worldwide public health issue that kills more than 5.7 million people per year and is a leading cause of disability.[12] Stroke increases the expression of matrix metalloproteinases, to promote the breakdown of the blood brain barrier, to increase brain swelling or edema and to enhance the risk of hemorrhage. In patients with stroke, 90% of the deaths within the first week are due to neurological causes such as brain swelling and hemorrhage.[15-17] Strokes with large amounts of cerebral edema are considered malignant or massive because they can cause increased intracranial pressure and loss of consciousness. Increased intracranial pressure resulting from edema and/or bleeding is associated with a high mortality and may lead to herniation.[18,19] The finding of significant brain swelling signifies a bad prognosis for patients, while measurements of infarct size have not been considered to be significant clinical predictors of disability.[20,21]

Tissue plasminogen activator (TPA) catalyzes the production of the blood clot-dissolving enzyme plasmin and is the only FDA-approved treatment for stroke. Unfortunately, the therapeutic benefit of TPA appears to be limited by its harmful or neurotoxic effects. TPA reduces disability in only 11-13% of treated patients.[22-24] TPA also significantly increases the risk of breakdown of the blood brain barrier resulting in brain hemorrhage which occurs in a dose-related fashion.[25] Administration of TPA to patients after prolonged ischemia may increase mortality.[26]

TPA is expressed by endothelial cells and by neurons and, thus is present both in the vascular space and the brain parenchyma.[27] Levels of endogenous TPA rise in the brain in response to injury.[28-30] In models of mechanical (non-thrombotic) occlusion of the middle cerebral artery (MCA), endogenous TPA increases neuronal cell death and pharmacologic administration of TPA further enhances brain injury.[31-33] Neuronal damage after a cerebral infarct is thought to be mediated in part by excitotoxins.[27] It has been shown that TPA enhances excitotoxic brain injury[34] through a plasminogen-dependent mechanism and that SerpinF2 (also known as $\alpha$2-antiplasmin), the serine protease inhibitor (serpin) of plasmin is protective.[35-37] Taken together, these data in mechanical occlusion models indicate that TPA exerts neurotoxic effects on the brain through its production of plasmin and, inhibition of plasmin activity by SerpinF2 reduces neurotoxicity. Yet paradoxically, for human ischemic stroke, which is typically caused by thrombotic (non-mechanical) occlusion, SerpinF2 is a risk factor which suggests that it may exerts negative effects.[38,39]

In addition to the brain, endogenous or administered TPA has harmful effects after ischemia in other tissues throughout the body. After ischemia in the kidneys, TPA increases tissue damage.[40] In a similar manner, after ischemia in the lungs, TPA enhances lung injury and diminishes lung function.[41] TPA has also been shown to increase myocyte tissue damage after cardiac ischemia.[42] Similar to its harmful effects on neurons, TPA also enhances retinal cell damage induced by excitotoxins in the eye.[43]

U.S. Pat. No. 6,946,438 to Nagai et al. provides the use of compounds, such as plasmin, mini-plasmin and micro-plasmin, that reduce a2-antiplasmin (SerpinF2) concentration or activity in vivo, for the treatment of focal cerebral ischemia infarction induced in animals by mechanical occlusion. However, mechanical occlusion does not simulate human ischemic stroke, which is predominantly caused by thrombosis or embolism of a clot (thromboembolism). The presence of a thrombus is associated with fibrin products and activation of platelets and the coagulation system, which may affect the ischemic microvasculature, trigger downstream thrombosis and have neurotoxic effects on neurons and other cells.[44]. It has been found that mechanical occlusion induces a different pattern of cellular injury associated with TPA than that caused by thrombotic occlusion.[30,44-46] For example, Nagai et al. found contradictory results for PAI-1 transgenic mice in a mechanical occlusion and in a thrombotic stroke occlusion model.[30] Since studies by these same authors suggest that compounds that reduce focal ischemia infarction induced by mechanical occlusion can have opposite effects on ischemic stroke induced by thrombosis, it is not predictable whether compounds described by Nagai et al. in U.S. Pat. No. 6,946,438 will reduce neuronal cell death triggered by thrombotic occlusion. In addition in U.S. Pat. No. 6,946,438, Nagai et al. do not teach whether such compounds may prevent disability, brain swelling, hemorrhage or death after ischemic stroke. Since mechanical occlusion does not simulate thrombotic stroke and does not adequately predict the value of potential therapies, there is a need to develop a composition and method of preventing or reducing cellular damage, swelling, edema and hemorrhage in ischemic conditions caused by thrombosis, such as thromboembolic stroke.

SUMMARY OF THE INVENTION

The present invention provides methods and compositions for inhibiting hemorrhage, organ edema, prolonged ischemia, breakdown of the microvascular barrier, apoptosis or TPA toxicity in a patient, comprising administering to the patient an effective amount of a SerpinF2-binding molecule that reduces SerpinF2 activity or concentration. The present methods of inhibition include methods for the prevention and treatment of the conditions described herein.

The invention also provides methods for the manufacture of a medicament for the treatment of all of the conditions described herein. The present invention provides that in various embodiments the SerpinF2-binding molecule is a SerpinF2 inhibitor selected from an antibody, a peptide, a DNA aptamer or a small molecule. In certain embodiments, the SerpinF2 inhibitor is an antibody. In certain embodiments, the SerpinF2 inhibitor is administered in a dose range from 28-91 nanomoles/kg.

In particular, the present invention provides a method of inhibiting functional disability or death from hemorrhage or edema in a patient in need thereof comprising administering to the patient an effective amount of a SerpinF2-binding molecule that reduces SerpinF2 activity or concentration, thereby inhibiting disability or death from hemorrhage or edema in the patient. In certain embodiments, the hemorrhage or edema is neurologic, cardiac, hepatic, pancreatic, respiratory or renal.

The present invention provides a method of inhibiting disability or death from tissue plasminogen activator (TPA) toxicity in a patient in need thereof comprising administering to said patient an effective amount of a SerpinF2-binding molecule that reduces SerpinF2 activity or concentration, thereby inhibiting disability or death from TPA toxicity. In certain embodiments, the TPA toxicity causes hemorrhage, organ edema, or apoptosis. In certain embodiments, the invention comprises the earlier step of determining that the patient is at risk for TPA induced damage. In certain embodiments, the TPA toxicity is due to ischemia or trauma. The invention provides that the TPA toxicity can cause neurologic, cardiac, hepatic, pancreatic, respiratory or renal damage. In certain embodiments, TPA toxicity is assessed by determining that TPA has been previously administered to the patient within 48 hours. In certain embodiments, a plasminogen activator or serine protease enzyme has been previously administered to the patient within 48 hours.

The invention provides a method of preventing apoptosis in a patient in need thereof comprising, administering to the patient an effective amount of a SerpinF2-binding molecule that diminishes SerpinF2 activity or concentration, thereby preventing apoptosis in the patient. In certain embodiments, the apoptosis occurs in neurologic, cardiac, hepatic, pancreatic, lung or renal cells.

The invention provides a method of inhibiting prolonged ischemia in a patient in need thereof comprising administering to said patient an effective amount of a SerpinF2-binding molecule that reduces SerpinF2 concentration or activity in said patient so as to inhibit the prolonged ischemia. In certain embodiments, the prolonged ischemia has been present for at least forty (40) minutes. In certain embodiments, the prolonged ischemia occurs in neurologic, cardiac, hepatic, pancreatic, lung or renal tissues. In certain embodiments, the method comprises the earlier step of determining that the patient has neurologic symptoms indicative of neuronal damage. In certain embodiments, the neurologic symptoms are classified as greater than or equal to Rankin 1 or NIH Stroke Scale 4.

BRIEF DESCRIPTION OF THE DRAWINGS

Middle cerebral artery (MCA) thromboembolism reduces hemispheric blood flow and causes neuronal cell death. (FIG. 1A) Hemispheric blood flow after MCA thromboembolism (arrow) as measured by laser Doppler. Thromboembolus (arrow) in the MCA as viewed from the base of the brain (FIG. 1B).

Figure 2A:
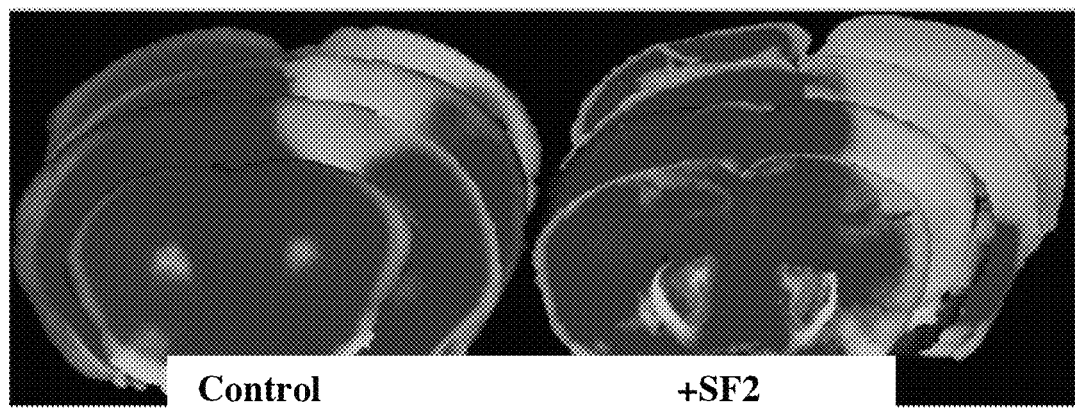
Figure 2B:
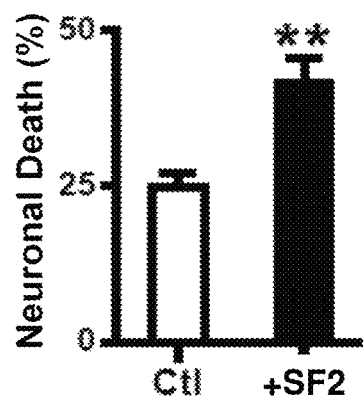
Figure 2C:
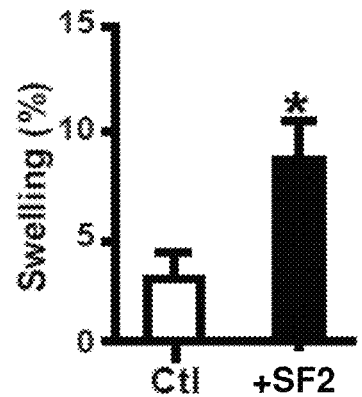

SerpinF2 causes neuronal cell death and brain swelling. Mice treated with SerpinF2 (SF2) or nothing (control) experienced ischemia induced by thromboembolism (FIG. 2A). Neuronal cell death as assessed by TTC staining in controls and SF2-treated mice. Neuronal cell death measured as percent of hemispheric brain volume. (*$p<0.01$ vs. control, FIG. 2B). Brain swelling as percent of the brain hemisphere. (*$p<0.05$ vs. control, FIG. 2C).

Figure 3A:
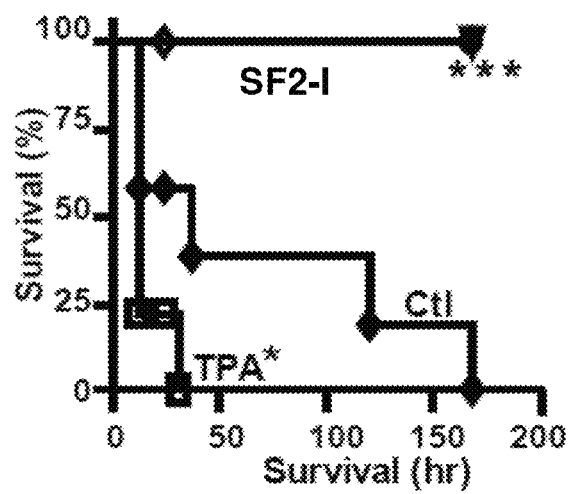
Figure 3B:
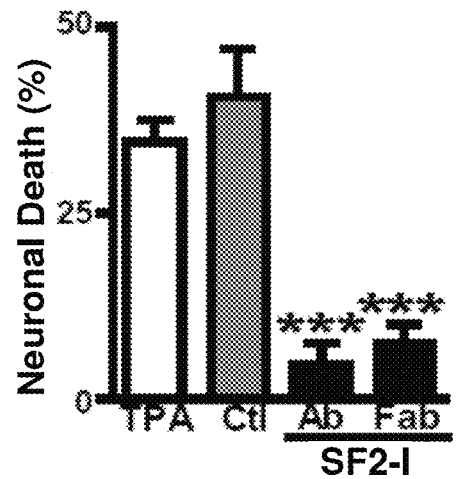
Figure 3C:
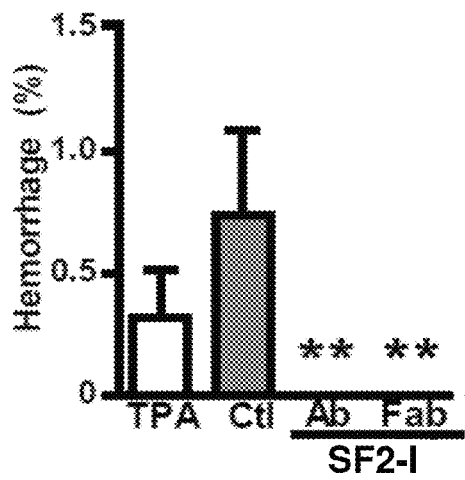
Figure 3D:
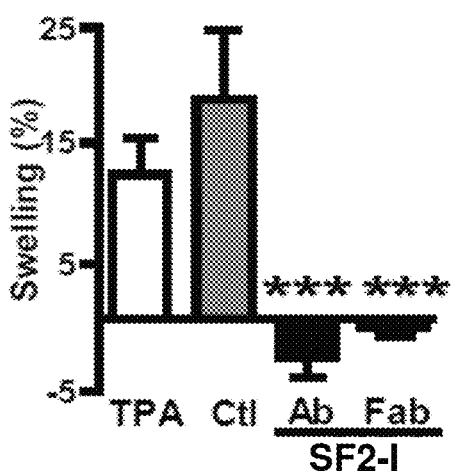
Figure 3E:
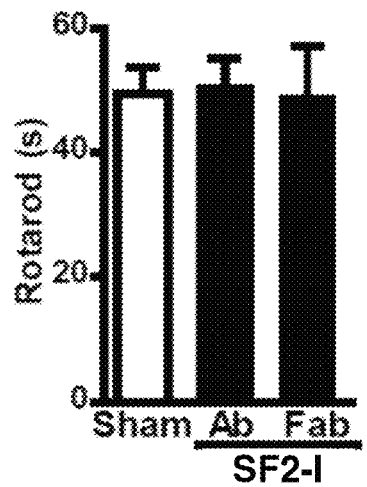

Agents that inhibit or inactivate SerpinF2 (SF2-I) reduce mortality, neuronal injury, edema, hemorrhage and disability. FIG. 3A) SF2-I in the form of whole antibody (Ab) or Fab fragments prevent death by comparison to control or TPA-treated mice. (*$p<0.0005$ vs TPA; $p<0.005$ vs. control). FIG. 3B) SF2-I reduce neuronal cell death (measured as percent of hemispheric volume; $p<0.001$ vs control or TPA). FIG. 3C) SF2-I prevent hemorrhage. ($p<0.01$ vs control; $p<0.05$ vs. TPA). FIG. 3D) SF2-I prevent brain swelling or edema. (*$p<0.001$ vs control; $p<0.05$ vs. TPA). FIG. 3E) SF2-I prevent behavioral disability by comparison to sham mice without strokes. Disability was measured by performance on a Rotarod.

Figure 4A:
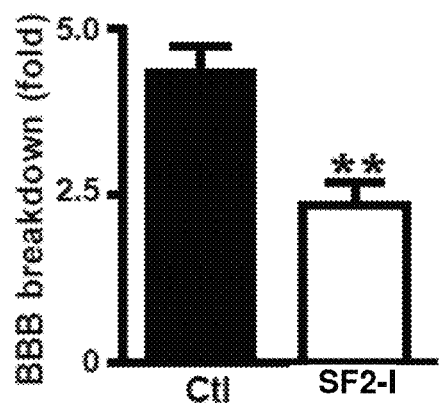
Figure 4B:
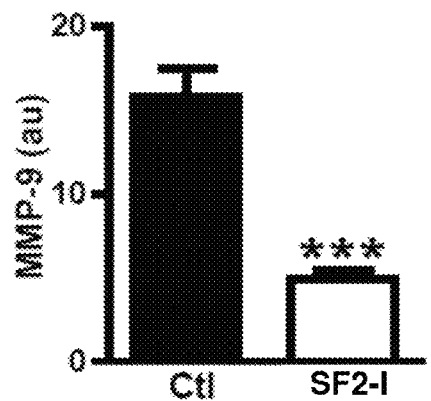
Figure 4C:
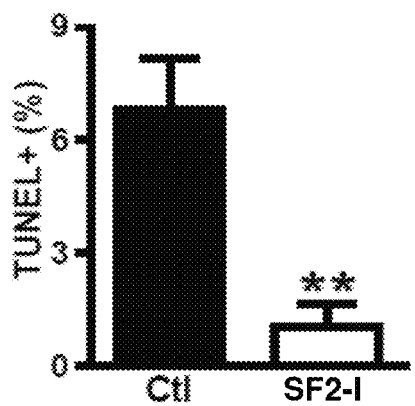
Figure 4D:
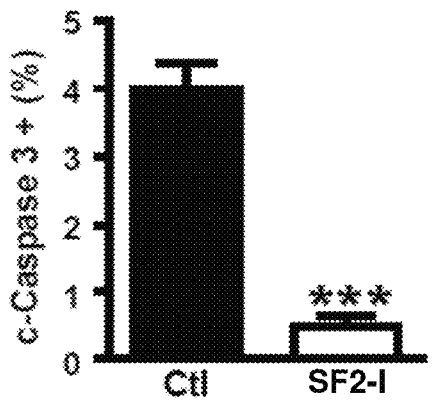

Agents that inhibit or inactivate SF2 (SF2-I) prevent breakdown of the blood brain barrier (BBB) (FIG. 4A), MMP-9 expression (FIG. 4B) and apoptosis as measured by TUNEL-staining (FIG. 4C) or caspase 3 cleavage (FIG. 4D). ($p<0.01$, *$p<0.001$ SF2-I vs. controls).

Figure 5A:
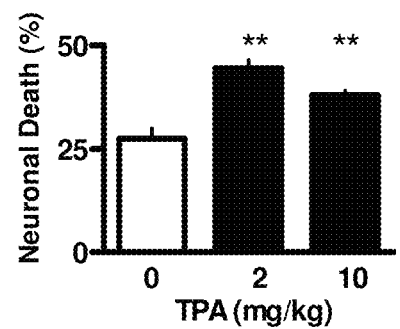
Figure 5B:
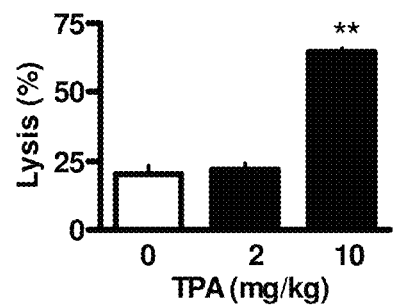
Figure 5C:
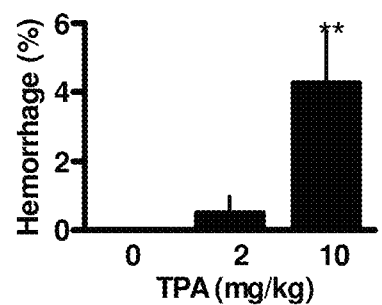

Neurotoxic effects of TPA on ischemic brains despite successful lysis. Mice were treated with standard dose TPA (10 mgs) or low dose TPA (2 mgs) after 2.5 hrs. of ischemia induced by thromboembolism. FIG. 5A) Neuronal cell death measured as percent of hemispheric brain volume. FIG. 5B) Percent lysis or dissolution of the thromboembolus. FIG. 5C) Brain hemorrhage assessed as the percent of hemispheric brain volume (**$p<0.01$ vs. control).

Figure 6A:
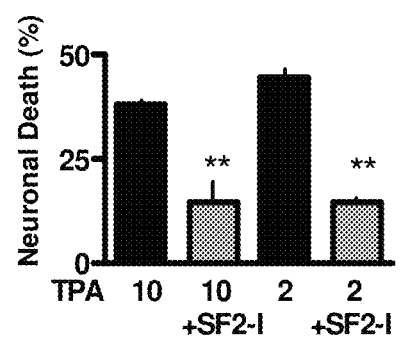
Figure 6B:
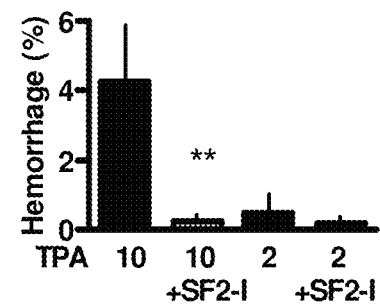

Agents that inhibit or inactivate SF2 (SF2-I) abrogate the neurotoxic effects of TPA to reduce neuronal cell death and hemorrhage. After 2.5 hours of ischemia induced by thromboembolism, mice were treated with standard (10 mg/kg) or low dose (2 mg/kg) TPA with or without a SerpinF2-inhibitor (SF2-I). FIG. 6A) Neuronal cell death measured as percent of hemispheric brain volume. FIG. 6B) Brain hemorrhage assessed as the percent of hemispheric brain volume (**$p<0.01$ TPA alone vs. TPA+SF2-I).

Figure 7A:
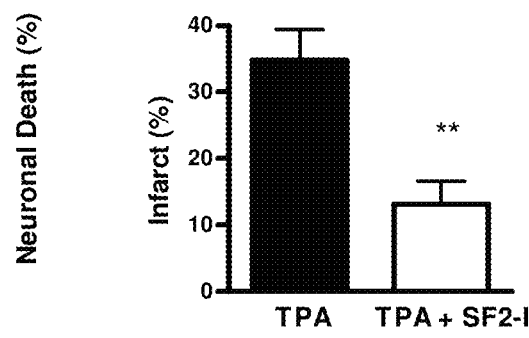
Figure 7B:
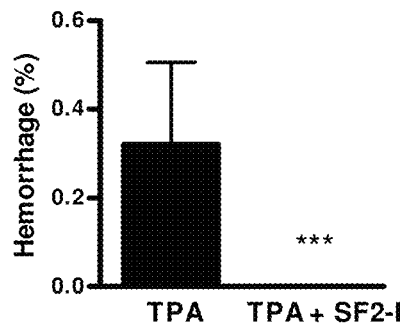
Figure 7C:
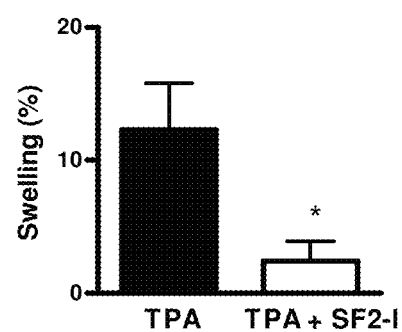

Agents that inhibit or inactivate SF2 (SF2-I) abrogate the neurotoxic effects of TPA to reduce neuronal cell death, hemorrhage and brain swelling in stroke survivors. After thromboembolic stroke, mice were treated with TPA alone (10 mg/kg) or TPA (2 mg/kg) with an SF2-inhibitor. FIG. 7A) Neuronal cell death measured as percent of hemispheric brain volume. FIG. 7B) Brain hemorrhage assessed as the percent of hemispheric brain volume. FIG. 7C) Brain swelling as a percent of hemispheric volume. (*p<0.05, p<0.01 or *p<0.001 TPA alone vs. TPA+SF2-I).

Figure 8A:
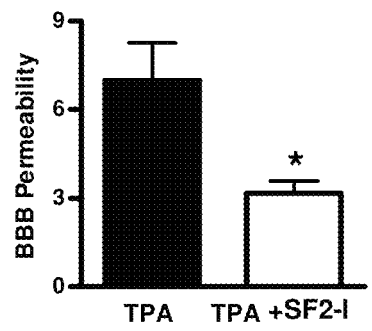
Figure 8B:
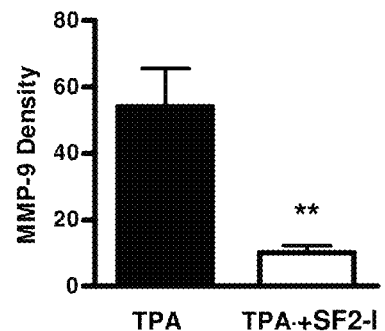
Figure 8C:
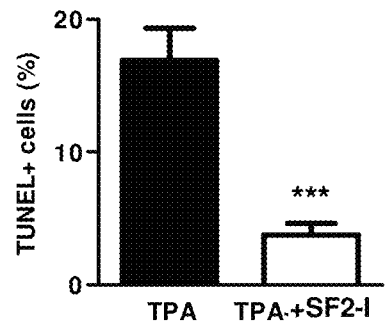

Agents that inhibit or inactivate SF2 (SF2-I) abrogate the neurotoxic effects of TPA to prevent breakdown of the blood brain barrier (BBB) (FIG. 8A), MMP-9 expression (FIG. 8B) and apoptosis measured by TUNEL-staining (FIG. 8C). (*p<0.05, p<0.01, *p<0.001 TPA vs. TPA+SF2-I).

DETAILED DESCRIPTION OF THE INVENTION

The present invention may be understood more readily by reference to the following detailed description of the preferred embodiments of the invention and the Examples included herein. However, before the present compounds, compositions, and methods are disclosed and described, it is to be understood that this invention is not limited to specific polypeptides, specific nucleic acids, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

It must be noted that as used herein and in the appended claims, the singular forms "a," "an," and "the," include plural forms unless the context clearly indicates otherwise. Thus, for example, reference to "an agent" includes one or more of such different agents, and reference to "the method" includes reference to equivalent steps and methods known to those of ordinary skill in the art that could be modified or substituted for the methods described herein.

Unless otherwise defined, all technical and scientific terms used herein have the meaning as commonly understood by one of ordinary skill in the art to which this invention belongs. The practice of the present invention employs, unless otherwise indicated, conventional techniques of cell biology, molecular biology, genetics, chemistry, microbiology, recombinant DNA, and immunology. See, for example, Maniatis et al. (1982) Molecular Cloning, A Laboratory Manual, latest edition, Cold Spring Harbor Laboratory, Cold Spring Harbor, N.Y.; Sambrook et al. (1989) Molecular Cloning: A Laboratory Manual, latest edition (Cold Spring Harbor, N.Y.: Cold Spring Harbor Laboratory Press); Ausubel et al. (1992) Current Protocols in Molecular Biology, latest edition (New York: John Wiley & Sons); Guthrie & Fink (1991) Methods Enzymol. 194:1-863; Cell Biology, A Laboratory Manual, ed. Celis, J. E., Academic Press, NY; Histochemistry, Pearse, A. G. E., Vol. 1 (1980), Vol. 2 (1985), and Vol. 3 (1990).

The present invention provides methods for inhibiting hemorrhage, organ edema, prolonged ischemia, breakdown of the microvascular barrier, apoptosis or TPA toxicity in a patient, comprising administering to the patient an effective amount of a SerpinF2-binding molecule that reduces SerpinF2 activity or concentration. The present methods of inhibition include methods for the prevention and treatment of the conditions described herein.

The invention also provides methods for the manufacture of a medicament for the treatment of the conditions described herein. The present invention provides that in various embodiments the SerpinF2-binding molecule is a SerpinF2 inhibitor selected from an antibody, a peptide, a DNA aptamer or a small molecule. In certain embodiments, the SerpinF2 inhibitor is an antibody. SerpinF2 inhibitors by directly binding to active sites on SerpinF2, or indirectly by binding other regions of SerpinF2 to sequester or otherwise reduce or diminish SerpinF2 activity, and thereby reduce the cellular damage associated with TPA toxicity. In certain embodiments, the SerpinF2 inhibitor is administered in a dose range from 28-91 nanomoles/kg.

In particular, the present invention provides a method of inhibiting functional disability or death from hemorrhage or edema in a patient in need thereof comprising administering to the patient an effective amount of a SerpinF2-binding molecule that reduces SerpinF2 activity or concentration, thereby inhibiting disability or death from hemorrhage or edema in the patient. In certain embodiments, the hemorrhage or edema is specific to any one or more of neurologic, cardiac, hepatic, pancreatic, respiratory or renal tissue.

The invention provides a method of preventing apoptosis in a patient in need thereof comprising, administering to the patient an effective amount of a SerpinF2-binding molecule that diminishes SerpinF2 activity or concentration, thereby preventing apoptosis in the patient. In certain embodiments, the apoptosis occurs in any one or more of neurologic, cardiac, hepatic, pancreatic, lung or renal cells.

The present invention provides a method of inhibiting disability or death from tissue plasminogen activator (TPA) toxicity in a patient in need thereof comprising administering to said patient an effective amount of a SerpinF2-binding molecule that reduces SerpinF2 activity or concentration, thereby inhibiting disability or death from TPA toxicity. In certain embodiments, the TPA toxicity causes hemorrhage, organ edema, or apoptosis. In certain embodiments, the invention comprises the earlier step of determining that the patient is at risk for TPA induced damage. In various embodiments, the TPA toxicity is, or is not, related to ischemia or trauma. The invention provides that the TPA toxicity can cause neurologic, cardiac, hepatic, pancreatic, respiratory or renal damage. In certain embodiments, TPA toxicity is assessed by determining that TPA has been previously administered to the patient within 48 hours. In certain embodiments, a plasminogen activator or serine protease enzyme has been previously administered to the patient within 48 hours.

The invention provides a method of inhibiting prolonged ischemia in a patient in need thereof comprising administering to said patient an effective amount of a SerpinF2-binding molecule that reduces SerpinF2 concentration or activity in said patient so as to inhibit the prolonged ischemia. In certain embodiments, the prolonged ischemia has been present for at least forty (40) minutes. In certain embodiments, the ischemia has been prolonged for at least fifty (50) minutes, one (1) hour, two (2) hours, three (3) hours, four (4) hours, five (5) hours, and longer. In certain embodiments, the prolonged ischemia occurs in any of neurologic, cardiac, hepatic, pancreatic, lung or renal tissues. In certain embodiments, the method comprises the earlier step of determining that the patient has neurologic symptoms indicative of neuronal damage. In certain embodiments, the neurologic symptoms are classified as greater than or equal to Rankin 1 or NIH Stroke Scale 4. Therefore, in certain embodiments, the invention also prolongs the time window for effective treatment in a patient with ischemia.

In certain embodiments, the hemorrhage, organ edema, prolonged ischemia, breakdown of the microvascular barrier, apoptosis or TPA toxicity results from ischemia. In certain embodiments, the invention comprises the earlier step of determining that the ischemia is due to a thrombotic ischemic stroke. In certain embodiments, the invention further comprises the earlier step of determining that the ischemia is not due to a mechanical occlusion. In certain embodiments, the hemorrhage, organ edema, prolonged ischemia, breakdown of the microvascular barrier, apoptosis or TPA toxicity are not in brain tissues and result from a condition other than stroke.

The present invention also provides compositions and methods of use thereof, of decreasing neuronal damage, functional disability or mortality in a patient associated with a prolonged ischemia at risk for the neurotoxicity induced by either an endogenous or externally administered plasminogen activator such as tissue plasminogen activator (TPA). The present disclosure describes for the first time that SerpinF2-binding agents and/or molecules, e.g., SerpinF2 inhibitors, can be used for reducing the cellular toxicity of tissue plasminogen activator (TPA) in thromboembolic stroke or ischemic damage caused by blood clots in brain as well as in other organs.

Reducing cellular damage in ischemia can be performed on any tissues in need, including without limitation tissues of the central or peripheral nervous system, hepatic/splenic/reticuolendothelial system, kidney and genitourinary system, cardiovascular system, respiratory system, endocrine system, skin, gastrointestinal system, neurosensory system musculoskeletal system, and hematopoietic-lymphatic system.

As used herein, a SerpinF2-binding agent or molecule can include, among other molecules, antibodies (polyclonal or monoclonal). The term "antibody" (Ab) or "monoclonal antibody" (MAb) is meant to include intact molecules as well as antibody fragments (such as, for example, $F_v$, $F_{ab}$ and $F_{(ab')2}$ fragments), single chain antigen-binding proteins, "humanized" antibodies, and chimeric antibodies which are capable of specifically binding to SerpinF2. $F_{ab}$ and $F_{(ab')2}$ fragments lack the $F_c$ fragment of intact antibody, clear more rapidly from the circulation, and may have less non-specific tissue binding of an intact antibody.

U.S. Pat. No. 6,114,506 and pending U.S. Publication No. 20100086536 to Reed et al. disclose certain other uses for SerpinF2 (aka, a2-antiplasmin) binding molecules, including but not limited to MAb 49C9, 70B11, 77A3, and RWR, all of which molecules are herein incorporated by reference. Further exemplary SerpinF2-binding molecules include the following commercially available antibodies: monoclonal antibodies to MAP4H9 (Molecular Innovations), 27C9 (Molecular Innovations), 14AP (Fitzgerald Industries), MPW14AP (antibodies-online GmbH), 3617 (American Diagnostics), goat polyclonal antibody to SerpinF2 (Biopool), and other anti-human polyclonal and monoclonal antibodies to SerpinF2 available from Genetex, Thermo Scientific Pierce Protein Research Products. The invention also contemplates the use of humanized and human antibodies constructed through molecular biology techniques.

The phrases "SerpinF2-binding" and "specifically binding" refer to a binding reaction that is determinative of the presence of the polypeptide in a heterogeneous population of polypeptides and other biologics. Thus, under designated immunoassay conditions, the specified antibodies (or other binding agent) bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual," latest edition, Cold Spring Harbor Publications, New York, (1988), for a description of immunoassay formats and conditions that could be used to determine selective binding.

The antibodies of the present invention may be prepared by any of a variety of methods. For example, cells expressing SerpinF2 (or fractions, lysates, etc. thereof) can be administered to an animal in order to induce the production of sera containing polyclonal antibodies that are capable of binding SerpinF2. In a preferred method, a preparation of SerpinF2 antibody of the present invention is prepared and purified to render it substantially free of natural contaminants. Such a preparation is then introduced into an animal in order to produce polyclonal antisera of greater specific activity.

The antibodies of the present invention may also be prepared using phage display technology. Methods of preparing antibodies using phage display are known in the art. See, for example, U.S. Pat. No. 5,565,332; Clarkson et al., 1991, *Nature* 352:624-628; Huse, 1989, *Science* 246:1275-1281; Kang, 1993, *Proc. Natl. Acad. Sci. USA* 88:11120-11123; Marks, 1991, *J. Mol. Biol.* 222:581-597; and McCafferty et al., 1990, *Nature* 348:552-554.

In some instances, it is desirable to prepare monoclonal antibodies (SerpinF2-binding molecules) from various hosts. A description of techniques for preparing such monoclonal antibodies may be found in Stites et al. eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988. For example, monoclonal antibodies can be prepared using hybridoma technology. In general, such procedures involve immunizing an animal (preferably a mouse) with the antigen or with a cell which expresses the antigen. A preferred antigen is purified SerpinF2 or a fragment thereof. Suitable cells can be recognized by their capacity to secrete anti-SerpinF2 antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 ug/1 of nonessential amino acids, about 1,000 U/ml of penicillin, and about 100 ug/ml of streptomycin. The splenocytes of such mice are extracted and fused with a suitable myeloma cell line. The method of somatic cell fusion is described in Galfre, G. and Milstein, C., Meth. Enzymol. 73:3-46 (1981). After fusion, the resulting hybridoma cells are selectively maintained in HAT medium, and then cloned by limiting dilution as described by Wands et al., 1981, Gastroenterology 80:225-232. The hybridoma cells obtained through such a selection are then assayed to identify clones which secrete antibodies capable of binding SerpinF2.

Alternatively, additional antibodies capable of binding to the SerpinF2 antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, SerpinF2-specific antibodies are used to immunize an animal, preferably a mouse. The splenocytes of such an animal are then used to produce hybridoma cells, and the hybridoma cells are screened to identify clones which produce an antibody whose ability to bind to the SerpinF2-specific antibody can be blocked by the SerpinF2 antigen. Such antibodies comprise anti-idiotypic antibodies to the SerpinF2-specific antibody and can be used to immunize an animal to induce formation of further SerpinF2-specific antibodies.

It will be appreciated that Fab and $F_{(ab')2}$ and other fragments of the antibodies of the present invention may be used according to the methods disclosed herein. Such fragments are typically produced by proteolytic cleavage, using enzymes such as papain (to produce $F_{ab}$ fragments) or pepsin (to produce $F_{(ab')2}$ fragments). Alternatively, SerpinF2-binding fragments can be produced through the application of recombinant DNA technology, through synthetic chemistry, or biotinylation.

Also intended within the scope of the present invention are humanized or chimeric antibodies, produced using genetic constructs derived from hybridoma cells producing the MAbs described above. Humanized antibodies are antibodies in which the framework or other regions of the murine Ab is replaced with the homologous regions of a nonmurine antibody. Chimeric antibodies are antibodies in which the murine constant region has been replaced with a non-murine constant region. Methods for production of chimeric antibodies are known in the art. See, for review: Morrison, Science, 229:1202-1207 (1985); Oi et al., Bio-Techniques 4:214 (1986); see also, Cabilly et al., U.S. Pat. No. 4,816,567 (Mar. 28, 1989); Taniguchi et al., EP171496 (Feb. 19, 1986); Morrison et al., EP173494 (Mar. 5, 1986); Neuberger et al., WO8601533 (Mar. 13, 1986); Robinson et al., WO 8702671 (May 7, 1987); Boulianne et al., Nature 312:643-646 (1984); and Neuberger et al., Nature 314:268-270 (1985). Methods for production of humanized antibodies are known in the art. See, for example, U.S. Pat. No. 5,585,089; Jones et al., Nature 321:522-525 (1986); and Kettleborough et al., Protein Engineering 4:773-783 (1991).

Also provided in the present invention are antibodies capable of binding to both (1) human and nonhuman circulating SerpinF2 and (2) human and nonhuman fibrin cross-linked SerpinF2. Such antibodies are well known in the art. See, for example, U.S. Pat. Nos. 4,946,778; 5,260,203; 5,091,513; and 5,455,030, all of which are herein incorporated by reference. Also intended within the scope of the present invention are variants of the antibodies described above.

Also provided in the present invention are SerpinF2-binding agents or molecules which are specifically not antibodies or fragments thereof. Screening for such SerpinF2-binding agents or molecules is routine in the art. Particular known compounds of interest or libraries of compounds generated through combinatorial chemistry techniques, for example, can be screened for the desired binding and conversion activity. Furthermore, phage display technology can be used to identify peptides, for example, for the desired binding and conversion activity. In general, phage display describes a selection technique in which a library of variants of a peptide or protein is expressed on the outside of a phage virion, while the genetic material encoding each variant resides on the inside (Sidhu et al., 2003, Chembiochem. 4:14; Ferrer et al., 1999, J. Pept. Res.: 54, 32; BouHamdan et al., 1998, J. Biol. Chem. 273: 8009). This creates a physical linkage between each variant protein sequence and the DNA encoding it, which allows rapid partitioning based on binding affinity to a given target molecule by an in vitro selection process called panning (Whaley et al., 2000, Nature, 405, 665). In its simplest form, panning is carried out by incubating a library of phage-displayed peptides with a plate (or bead) coated with the target, washing away the unbound phage, and eluting the specifically bound phage. The eluted phage is then amplified and taken through additional binding/amplification cycles to enrich the pool in favor of binding sequences. After 3-4 rounds, individual clones are characterized by DNA sequencing and ELISA. Many variations of the phage display technology are known to those of skill in the art which can be adapted for purposes of the present invention.

In one embodiment, a phage display peptide library is used such as provided by New England Biolabs (Mass, MA). The pre-made random peptide libraries, Ph.D. libraries, have been used for myriad similar applications, including epitope mapping, identification of protein-protein contacts (Rozinov and Nolan, 1998, Chem. Biol. 5:713-28) and enzyme inhibitors (Rodi et al., 1999, J. Mol. Biol. 285:197-203).

As used herein, the term "patient" is intended to be human or nonhuman. Preferably, the patient is human. As used herein the term "administering" refers to various means of introducing a composition into a cell or into a patient. These means are well known in the art and may include, for example, injection or infusion for parenteral delivery; tablets, pills, capsules, or other solids for oral administration; nasal solutions or sprays; aerosols; inhalants; topical formulations; liposomal forms; and the like. As used herein, the terms "effective amount" and "therapeutic amount" refer to an amount that will result in the desired result and may readily be determined by one of ordinary skill in the art depending upon the specific activity of the chosen SerpinF2 inhibitor and the condition of the patient. In certain embodiments, an effective or therapeutic amount of a SerpinF2 inhibitor is in a dose range of 28-91 nanomole/kg, 4.2-13.65 mg/kg, or 0.5-1.0 moles inhibitor to mole of SerpinF2.

The compositions of the present invention may be formulated for various means of administration. As used herein, the term "route" of administration is intended to include, but is not limited to subcutaneous injection, intravenous injection, intraocular injection, intradermal injection, intramuscular injection, intraperitoneal injection, intratracheal administration, epidural administration, inhalation, intranasal administration, oral administration, sublingual administration, buccal administration, rectal administration, vaginal administration, and topical administration. The preparation of an aqueous composition that contains a peptide, antibody or antibody fragment, antisense nucleic acid, receptor decoy, ribozyme, sense polynucleotide, double stranded RNA, RNAi, aptamer, or small molecule agonist, as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The compositions of the present invention can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars, or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate, and gelatin.

Prior to or upon formulation, the compositions of the present invention should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filter sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the active ingredient admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that for human administration, preparations should meet sterility, pyrogenicity, and general safety and purity standards as required by FDA Office of Biological Standards.

Pharmaceutical compositions are provided that comprise an effective amount of a compound or molecule used in the disclosed methods for preventing and/or reducing cellular injury, neuronal damage, swelling, functional disability, mortality, and cerebral hemorrhage in a patient at risk for the neurotoxicity induced by either an endogenous or externally administered tissue plasminogen activator (TPA) associated with a prolonged ischemia, and/or associated with an activity of SerpinF2. Pharmaceutical compositions are also provided that comprise an effective amount of a compound or molecule used in the disclosed methods for decreasing neuronal damage, functional disability, mortality or hemorrhage by prolonging the time window for effective treatment in a patient with ischemia.

Prolonged ischemia, trauma or cause of brain injury is first manifested by neurologic symptoms which may include muscle weakness, altered speech, altered consciousness, seizure or other impairment of normal neurologic function. A physician or other suitably trained healthcare professional makes the determination of prolonged ischemic condition, trauma or a diagnosis of developing stroke, after interviewing and examining the patient. The diagnosis can be confirmed or refuted by arteriography, or CT, MRI or PET scanning or other imaging tests of the brain which may disclose evidence of arterial obstruction, brain hypoperfusion, infarction, neuronal cell damage, edema, etc. Additionally, diagnostic tests (e.g., imaging, EEGs, blood tests, etc.) can be used to identify conditions in which SerpinF2 inhibitors would be inappropriate, such as in cases of significant intracranial hemorrhage, non-ischemic seizures, etc. The invention provides for the administration of SerpinF2-binding agents after determination or diagnosis of prolonged ischemia, trauma or other injury to the brain which has resulted in neurologic symptoms and disability. Such disability can be assessed with clinical scales such as the Rankin scale, NIH Stroke Scale, Glasgow scale, etc.

The invention also provides for methods of administration of SerpinF2-binding agents prior to expected ischemia, trauma or injury, provided that the patient has been excluded from unacceptable bleeding risk. In such instances ischemia may be induced by occlusion of the cerebral vessels such as during carotid endarterectomy, following cerebral embolism complicating procedures on the heart or major arteries, or post heart valve surgeries, etc. It is understood that such determinations of the patients' ischemic condition involve physical transformations of matter and/or the use of medical equipment through the manipulation of the patient under examination and the performance of diagnostic tests.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Methods

MCA thromboembolism model.[47,48] Normal C57BL/6J adult mice (29-35 g) were obtained from The Jackson Laboratory (Bar Harbor, Me.). Mice were housed in microisolation cages on a constant 12-hour light/dark cycle with controlled temperature and humidity, and given access to food and water ad libitum. Experiments adhered to the guidelines set forth in the *Guide for the Care and Use of Laboratory Animals* (DHHS Publication No. (NIH) 85-23 Revised 1985) and were performed under protocols approved by the Medical College of Georgia's and the University of Tennessee's Institutional Animal Care and Use Committee. Mice were mechanically ventilated using 1.5 to 2% isoflurane and O2 during surgery as described using a TOPO Dual Mode Ventilator (Kent Scientfic, Torrington, Conn.).[49] Body temperature was maintained at 37° C. with a warming pad. Cerebral blood flow was monitored by a laser Doppler monitor with a fiber optic probe (ADInstruments PowerLab 2/26, blood flow meter ML191, OxyFlo Probe MSF100XP). The left common carotid artery was isolated after a neck incision, and the external carotid, thyroid, and occipital arteries were ligated. Microvascular clips were temporarily placed on the common carotid and internal carotid arteries. A small arteriotomy was made on the external carotid artery for retrograde insertion of the PE8 catheter containing the clot. Clots were made with pooled fresh frozen from normal mice mixed with $^{125}$I-fibrinogen (~100,000 cpm/20 ul, PerkinElmer NEX430110UC) and stained with Evans blue dye. The PE8 tube containing the clots was counted in a gamma-scintillation counter, inserted into the left external carotid artery, threaded into the ICA up towards the origin of the MCA and the thrombus was embolized at a speed of 0.45 mL/min in a volume of 100 ul saline. A Geiger-Muller counter was used to confirm appropriate embolization.

At the appropriate time post-embolism, TPA (Genentech, South San Francisco) was given by bolus (20% of dose) followed by infusion (80% of dose) over 30 min in saline in 300 ul via the contralateral jugular vein. In other experiments TPA and/or a SerpinF2 inhibitor (4H9, Molecular Innovations, Novi, MI), or SerpinF2 or saline (control) were administered via the contralateral jugular vein. After 4 hrs. of ischemia the animal was euthanized, citrated blood was isolated by cardiac puncture and tissues were perfused as we have described.[49] The brain was sectioned coronally into 2 mm sections and photographed to digitally image gross hemorrhage. The slices were incubated in TTC to identify viable tissue. In experiments investigating survival and disability after stroke, animals were administered the indicated agents at 30 min. or more after thromboembolism.

The hemispheric size, area of gross hemorrhage and area of neuronal injury were digitally analyzed by a blinded observer using Image Pro Plus 6.2 software and multiplied by the slice thickness to determine volume (mm)$^3$ using Swanson's method.[50] The mean volume was determined from at least 8 different measurements per brain. The means of the average values for each group were compared by a one way ANOVA with a Neuman Keuls correction. The amount of lysis was determined by comparison of the residual thrombus radioactivity in the brain to that of the initial clot as we have described.[51]

Plasminogen and fibrinogen levels were measured in plasma in duplicate after stroke as we have described.[52] The means of the average values for each group compared by a one way ANOVA with a Neuman Keuls correction.

Data Analysis

Statistical analyses were performed as described above and differences between groups were considered to be significant if P<0.05. Data are reported as mean±SEM.

Results

Thromboembolism typically reduced hemispheric blood flow by ~80% (FIG. 1A). Thromboemboli were readily detected in the proximal MCA (FIG. 1B) and there was blanching of the affected cortex (not shown). There were large areas of neuronal cell death in the thromboembolic group mice treated with placebo (controls) but no neuronal cell death in the sham group of mice that received no thromboemboli. There was significant fibrinolysis of the thromboembolus in the controls (20.6±2.5%) consistent with previous reports of enhanced endogenous TPA activity following stroke.[53,54]

In contrast to previous studies,[36] administration of SerpinF2 unexpectedly increased, rather than decreased, neuronal cell damage by comparison to controls. (p<0.01; FIGS. 3A, B). Administration of SerpinF2 significantly decreased lysis of the thromboembolus when compared to control mice or mice receiving the SerpinF2 inhibitor (p<0.01). Administration of SerpinF2 also markedly increased swelling or edema in the ischemic hemisphere, another unexpected finding (FIG. 3C, p<0.05). There was no cerebral hemorrhage detected in any of the control or SerpinF2-treated mice.

Treatment of mice with a SerpinF2 inhibitor markedly reduced mortality rates by comparison to TPA-treated mice (p<0.0005, FIG. 2a) or control mice (p<0.005, FIG. 3A). This effect was independent of the molecular form of the SerpinF2 inhibitor as both whole monoclonal antibody and Fab fragments saved lives by comparison to TPA (p<0.001, FIG. 3A) and to controls (p<0.01, FIG. 3A). The survival effect was also dose-dependent: lower doses of the SerpinF2 inhibitor were less effective than higher doses (p=0.05, not shown) but still reduced mortality by comparison to control and TPA (p=0.01). Microscopic examination of the brains of mice surviving the initial stroke period (≥12 hrs.) showed that SerpinF2 inactivation, whether in the form of a whole antibody or Fab, reduced neuronal cell death by comparison to control or TPA-treated mice (FIG. 3B, p<0.001). Inactivation of SF2 prevented brain hemorrhage when compared to control mice (FIG. 3C, p<0.01) or those receiving TPA (FIG. 3C, p<0.05). Inactivation of SerpinF2 by whole antibody or Fab prevented brain swelling by comparison to controls (FIG. 3D, p<0.001) and TPA-treated mice (FIG. 3D, p<0.05). To determine functional limitation after stroke, behavioral tests were performed after a week of recovery. Survival was markedly limited in control or TPA-treated mice, therefore sham mice that underwent the surgical procedure, but had no stroke, were used for comparison. By comparison to sham mice without stroke, treatment with an SF2-I prevented mice from disability as judged by their ability to maintain balance on a rotating cylinder (Rotarod), a standard behavioral test for mice after stroke (FIG. 3E).[55]

Normally, occlusion of the middle cerebral artery is associated with poor neurologic recovery, higher mortality and brain edema or swelling.[56] Brain swelling is attributed to breakdown of the blood brain barrier which permits movement of fluids from the blood into the brain tissue. Opening of the blood brain barrier is due in part to increases in endogenous TPA activity in the perivascular tissue after stroke.[57] Microscopic analyses of control brains showed that levels of albumin, a blood protein, were increased several fold on the side of the brain affected by stroke by comparison to the side of the brain without stroke (p<0.005) or by comparison to shams (p<0.001, not shown). Albumin staining was most intense in the perivascular area. By comparison to controls, inhibition of SF2 significantly reduced albumin staining consistent with decreased blood brain barrier breakdown (FIG. 4A; p<0.01). MMP-9 contributes to breakdown of the blood brain barrier.[58] Levels of MMP-9 rise after stroke[58] and are associated with increased risk of hemorrhage in humans.[59] MMP-9 expression was often found in the area of astrocytes foot processes typically associated with the blood brain barrier. By comparison to control mice, inhibition of SF2 significantly reduced MMP-9 expression (FIG. 4B; p<0.001). Since inhibition of SF2 reduced neuronal cell death, MMP-9 expression and breakdown of the blood brain barrier, it may also decrease brain cell death associated with apoptosis. Consistent with this notion, the percent of TUNEL-stained cells was significantly decreased in mice treated with the SF2-inactivator by comparison to controls (FIG. 4C, p<0.01). In addition, staining for cleaved caspase 3, a more specific indicator of apoptosis, was also reduced in the mice treated with an SF2-inactivator (FIG. 4D; p<0.001).

TPA is currently the only FDA-approved treatment for ischemic stroke. Administration of a standard dose of TPA for mice (10 mg/kg) after 2.5 hrs. of ischemia, which simulates the typical treatment time of human stroke, significantly increased neuronal cell death by comparison to control (p<0.01, FIG. 5A), indicating that TPA enhanced neuronal injury. The standard dose of TPA also significantly increased dissolution of the thromboembolus (p<0.01, FIG. 5B) and caused a marked increase in brain hemorrhage (p<0.05, FIG. 5C). Administration of a lower dose of TPA (2 mg/kg) after 2.5 hrs. of ischemia enhanced neuronal cell death when compared to control mice (p<0.01, FIG. 5A). The lower dose of TPA did not significantly increase the dissolution of the thrombus or increase hemorrhage (FIGS. 5B & C).

Previous studies had suggested that administration of SerpinF2 may reduce TPA-induced neurotoxicity.[35] Surprisingly, however, administration of standard dose TPA (10 mg/kg) with a SerpinF2 inhibitor markedly reduced neuronal damage by comparison to TPA alone (FIG. 6A, p<0.01). In a similar fashion, administration of low dose TPA with a SerpinF2 inhibitor significantly reduced neuronal damage when compared to low dose TPA alone (p<0.01). Finally, administration of standard dose TPA with a SerpinF2 inhibitor markedly reduced the hemorrhage caused by standard dose TPA alone (FIG. 6B, p<0.01).

Given that SerpinF2 appeared to enhance TPA's effect on neuronal cell death, it was examined whether an SF2-I could reduce TPA associated mortality after thromboembolic stroke. Mortality was 78% after TPA treatment but 0% when mice were treated with TPA and a SerpinF2 inhibitor (p=0.005). Treatment with TPA and a SerpinF2 inhibitor reduced neuronal cell death by comparison to TPA alone (FIG. 7A, p<0.01). Treatment with TPA and a SerpinF2 inhibitor also prevented hemorrhage by comparison to TPA alone (FIG. 7B, p<0.001). Finally, the combination of TPA and a SerpinF2 inhibitor significantly reduced hemispheric swelling by comparison to TPA alone (FIG. 7C, p<0.05) .Taken together, these studies show that SerpinF2 inhibition reverses the effects of endogenous and exogenous TPA and significantly increases survival after ischemic stroke. This appears to be related to the fact that Serpin F inhibition prevents hemorrhage and brain swelling which are major causes of mortality and disability after stroke.

Since inhibition of SF2 reduces TPA-induced hemorrhage it may also preserve the integrity of the blood brain barrier in TPA-treated mice. In mice treated with TPA alone, there was leakage of albumin outside vascular spaces identified by collagen IV immunostaining (FIG. 8A). In contrast, albumin leakage was markedly reduced in mice treated with TPA and the SF2-I (FIG. 8A, p<0.05), consistent with reduced breakdown of the blood brain barrier. Matrix metalloproteinase-9 has been identified as a key mediator in breakdown of the blood brain barrier, hemorrhage and brain edema after TPA therapy.[60,61] TPA-treated mice showed significantly greater expression of MMP-9 in the brain than control, untreated mice (p<0.01). Combination treatment with TPA and the SF2-I markedly reduced MMP-9 levels (FIG. 8B, p<0.01). TPA treatment also significantly enhanced TUNEL staining, consistent with enhanced apoptosis in the stroke region (FIG. 8C). By comparison, the combination of TPA and the SF2-I markedly reduced TUNEL staining (FIG. 8C, p<0.001), consistent with protection against apoptosis.

In mechanical occlusion and brain injury models TPA expression is enhanced after brain injury.[28-30] In these models, both endogenous and pharmacologic TPA are neurotoxic and SerpinF2 inhibitor reduces neurotoxicity.[31-33] Many different mechanisms have been proposed to explain TPA's neurotoxocity.[27,61] However, since the vast majority of human strokes are due to thrombotic or thromboembolic arterial occlusion, it has been argued that the neurotoxicity of TPA observed with non-thrombotic methods may have limited translational relevance to human ischemic stroke[62] where the actions of TPA in dissolving thrombi may be neuroprotective. To examine the overall neuroprotective and neurotoxic effects of TPA in a manner that has translational relevance to human stroke, the thromboembolic stroke model described by Zhang et al.[47] was modified. The result was a reproducible model of large vessel (MCA) thromboembolism that permits the simultaneous examination of neuronal cell death, hemorrhage, fibrinolysis and swelling after different periods of ischemia.

Most humans present with stroke after 2 or more hours of ischemia. When TPA treatment was given 2.5 hrs. after thromboembolism, i.e., at times that more closely simulate the timing of human therapy, it had neurotoxic effects. Despite successfully increasing the dissolution of the thromboemboli, TPA also significantly increased neuronal cell death and cerebral hemorrhage. Treatment with TPA also affected survival after thromboembolic stroke. Mice treated with TPA had significant mortality 24 hours after treatment (78%). These lethal, neurotoxic effects occurred despite clear evidence that TPA was inducing systemic plasminogen activation as indicated by plasminogen (p<0.01) and fibrinogen consumption (p<0.001).

Previous studies with mechanical occlusion indicate that SerpinF2 protects against the neurotoxicity of TPA.[36] Previous studies with SerpinF2 inhibitors show that they directly enhance TPA activity (U.S. Pat. No. 6,114,506). Increased TPA activity is associated with increased neuronal cell death, hemorrhage (FIG. 5), death (FIG. 3), breakdown of the blood brain barrier, increased MMP-9 expression and apoptosis (FIG. 6) after prolonged ischemia. Therefore, it is not expected that SerpinF2 inhibitors would markedly reduce these neurotoxic effects of TPA.

In summary, in a thromboembolic model of ischemic stroke, standard and low dose TPA caused neuronal cell death, with or without successful fibrinolysis, after prolonged ischemia. In contrast to previous predictions, treatment with an inhibitor of SerpinF2 markedly reduced the neurotoxicity of pharmacologic and endogenous TPA and enhanced survival after thromboembolic stroke.

REFERENCES

1. Dohmen C, Galldiks N, Bosche B, Kracht L, Graf R. The severity of ischemia determines and predicts malignant brain edema in patients with large middle cerebral artery infarction. Cerebrovasc Dis 2012; 33:1-7.
2. Westermaier T M, Stetter C M, Raslan F M, Vince G H M P, Ernestus R I M P. Brain edema formation correlates with perfusion deficit during the first six hours after experimental subarachnoid hemorrhage in rats. Exp Transl Stroke Med 2012; 4:8.

3. Martinet V, Guigui B, Glacet-Bernard A, et al. Macular edema in central retinal vein occlusion: correlation between optical coherence tomography, angiography and visual acuity. Int Ophthalmol 2012.
4. Abdel-Aty H, Cocker M, Meek C, Tyberg J V, Friedrich M G. Edema as a very early marker for acute myocardial ischemia: a cardiovascular magnetic resonance study. J Am Coll Cardiol 2009; 53:1194-201.
5. Garcia-Dorado D, Andres-Villarreal M, Ruiz-Meana M, Inserte J, Barba I. Myocardial edema: a translational view. J Mol Cell Cardiol 2012; 52:931-9.
6. Chen K H, Chao D, Liu C F, Chen C F, Wang D. Ischemia and reperfusion of the lung tissues induced increase of lung permeability and lung edema is attenuated by dimethylthiourea (PP69). Transplant Proc 2010; 42:748-50.
7. Greca F H, Goncalves N M, Souza Filho Z A, Noronha L, Silva R F, Rubin M R. The protective effect of methylene blue in lungs, small bowel and kidney after intestinal ischemia and reperfusion. Acta Cir Bras 2008; 23:149-56.
8. Lee H T, Park S W, Kim M, D'Agati V D. Acute kidney injury after hepatic ischemia and reperfusion injury in mice. Lab Invest 2009; 89:196-208.
9. Fujimoto K, Hosotani R, Wada M, et al. Ischemia-reperfusion injury on the pancreas in rats: identification of acinar cell apoptosis. J Surg Res 1997; 71:127-36.
10. Sage E, Mercier O, Van den Eyden F, et al. Endothelial cell apoptosis in chronically obstructed and reperfused pulmonary artery. Respir Res 2008; 9:19.
11. Bekkers S C, Yazdani S K, Virmani R, Waltenberger J. Microvascular obstruction: underlying pathophysiology and clinical diagnosis. J Am Coll Cardiol 2010; 55:1649-60.
12. Strong K, Mathers C, Bonita R. Preventing stroke: saving lives around the world. Lancet neurology 2007; 6:182-7.
13. Albers G W, Amarenco P, Easton J D, Sacco R L, Teal P. Antithrombotic and thrombolytic therapy for ischemic stroke: American College of Chest Physicians Evidence-Based Clinical Practice Guidelines (8th Edition). Chest 2008; 133:630 S-69S.
14. Fieschi C, Argentine C, Lenzi G L, Sacchetti M L, Toni D, Bozzao L. Clinical and instrumental evaluation of patients with ischemic stroke within the first six hours. Journal of the neurological sciences 1989; 91:311-21.
15. Viitanen M, Winblad B, Asplund K. Autopsy-verified causes of death after stroke. Acta Med Scand 1987; 222:401-8.
16. Bamford J, Dennis M, Sandercock P, Burn J, Warlow C. The frequency, causes and timing of death within 30 days of a first stroke: the Oxfordshire Community Stroke Project. J Neurol Neurosurg Psychiatry 1990; 53:824-9.
17. Braga P, Ibarra A, Rega I, et al. Prediction of early mortality after acute stroke. J Stroke Cerebrovasc Dis 2002; 11:15-22.
18. Silver F L, Norris J W, Lewis A J, Hachinski V C. Early mortality following stroke: a prospective review. Stroke 1984; 15:492-6.
19. Koennecke H C, Belz W, Berfelde D, et al. Factors influencing in-hospital mortality and morbidity in patients treated on a stroke unit. Neurology 2011; 77:965-72.
20. Johnston K C, Wagner D P, Wang X Q, et al. Validation of an acute ischemic stroke model: does diffusion-weighted imaging lesion volume offer a clinically significant improvement in prediction of outcome? Stroke 2007; 38:1820-5.
21. Saver J L, Johnston K C, Homer D, et al. Infarct volume as a surrogate or auxiliary outcome measure in ischemic stroke clinical trials. The RANTTAS Investigators. Stroke 1999; 30:293-8.
22. Marler J R, Goldstein L B. Medicine. Stroke—tPA and the clinic. Science 2003; 301:1677.
23. Alexandrov A V, Demchuk A M, Felberg R A, et al. High rate of complete recanalization and dramatic clinical recovery during tPA infusion when continuously monitored with 2-MHz transcranial doppler monitoring. Stroke 2000; 31:610-4.
24. Kwiatkowski T G, Libman R B, Frankel M, et al. Effects of tissue plasminogen activator for acute ischemic stroke at one year. National Institute of Neurological Disorders and Stroke Recombinant Tissue Plasminogen Activator Stroke Study Group. N Engl J Med 1999; 340:1781-7.
25. Levy D E, Brott T G, Haley E C, Jr., et al. Factors related to intracranial hematoma formation in patients receiving tissue-type plasminogen activator for acute ischemic stroke. Stroke 1994; 25:291-7.
26. Lees K R, Bluhmki E, von Kummer R, et al. Time to treatment with intravenous alteplase and outcome in stroke: an updated pooled analysis of ECASS, ATLANTIS, NINDS, and EPITHET trials. Lancet 2010; 375: 1695-703.
27. Vivien D, Buisson A. Serine protease inhibitors: novel therapeutic targets for stroke? J Cereb Blood Flow Metab 2000; 20:755-64.
28. Stehling F, Weber R, Ozcelik A, et al. Acute changes of coagulation and fibrinolysis parameters after experimental thromboembolic stroke and thrombolytic therapy. Neuroscience letters 2008; 441:39-43.
29. Dietzmann K, von Bossanyi P, Krause D, Wittig H, Mawrin C, Kirches E. Expression of the plasminogen activator system and the inhibitors PAI-1 and PAI-2 in posttraumatic lesions of the CNS and brain injuries following dramatic circulatory arrests: an immunohistochemical study. Pathology, research and practice 2000; 196:15-21.
30. Nagai N, Suzuki Y, Van Hoef B, Lijnen H R, Collen D. Effects of plasminogen activator inhibitor-1 on ischemic brain injury in permanent and thrombotic middle cerebral artery occlusion models in mice. J Thromb Haemost 2005; 3:1379-84.
31. Wang Y F, Tsirka S E, Strickland S, Stieg P E, Soriano S G, Lipton S A. Tissue plasminogen activator (tPA) increases neuronal damage after focal cerebral ischemia in wild-type and tPA-deficient mice. Nat Med 1998; 4:228-31.
32. Nagai N, De Mol M, Lijnen H R, Carmeliet P, Collen D. Role of plasminogen system components in focal cerebral ischemic infarction: a gene targeting and gene transfer study in mice. Circulation 1999; 99:2440-4.
33. Sheehan J J, Tsirka S E. Fibrin-modifying serine proteases thrombin, tPA, and plasmin in ischemic stroke: a review. Glia 2005; 50:340-50.
34. Tsirka S E, Gualandris A, Amaral D G, Strickland S. Excitotoxin-induced neuronal degeneration and seizure are mediated by tissue plasminogen activator. Nature 1995; 377:340-4.
35. Tsirka S E, Bugge T H, Degen J L, Strickland S. Neuronal death in the central nervous system demonstrates a non-fibrin substrate for plasmin. Proceedings of the National Academy of Sciences of the United States of America 1997; 94:9779-81.
36. Tsirka S E, Rogove A D, Bugge T H, Degen J L, Strickland S. An extracellular proteolytic cascade promotes neuronal degeneration in the mouse hippocampus. J Neurosci 1997; 17:543-52.
37. Yepes M, Sandkvist M, Coleman T A, et al. Regulation of seizure spreading by neuroserpin and tissue-type plasminogen activator is plasminogen-independent. J Clin Invest 2002; 109:1571-8.
38. Suri M F, Yamagishi K, Aleksic N, Hannan P J, Folsom A R. Novel hemostatic factor levels and risk of ischemic stroke: the Atherosclerosis Risk in Communities (ARIC) Study. Cerebrovasc Dis 2010; 29:497-502.
39. Marti-Fabregas J, Borrell M, Cocho D, et al. Hemostatic markers of recanalization in patients with ischemic stroke treated with rt-PA. Neurology 2005; 65:366-70.
40. Roelofs J J, Rouschop K M, Leemans J C, et al. Tissue-type plasminogen activator modulates inflammatory responses and renal function in ischemia reperfusion injury. J Am Soc Nephrol 2006; 17:131-40.
41. Zhao Y, Sharma A K, LaPar D J, et al. Depletion of tissue plasminogen activator attenuates lung ischemia-reperfusion injury via inhibition of neutrophil extravasation. Am J Physiol Lung Cell Mol Physiol 2011; 300:L718-29.
42. Hong T T, Huang J, Lucchesi B R. Effect of thrombolysis on myocardial injury: recombinant tissue plasminogen activator vs. alfimeprase. Am J Physiol Heart Circ Physiol 2006; 290:H959-67.
43. Kumada M, Niwa M, Wang X, et al. Endogenous tissue type plasminogen activator facilitates NMDA-induced retinal damage. Toxicol ApplPharmacol 2004; 200:48-53.
44. Del Zoppo G J. Focal cerebral ischemia and hemostasis: a PAI-1 conundrum. J Thromb Haemost 2005; 3:1376-8.
45. Aoki T, Sumii T, Mori T, Wang X, Lo E H. Blood-brain barrier disruption and matrix metalloproteinase-9 expression during reperfusion injury: mechanical versus embolic focal ischemia in spontaneously hypertensive rats. Stroke 2002; 33:2711-7.
46. Asahi M, Huang Z, Thomas S, et al. Protective effects of statins involving both eNOS and tPA in focal cerebral ischemia. J Cereb Blood Flow Metab 2005; 25:722-9.
47. Zhang Z, Chopp M, Zhang R L, Goussev A. A mouse model of embolic focal cerebral ischemia. J Cereb Blood Flow Metab 1997; 17:1081-8.
48. Zhang Z G, Zhang L, Ding G, et al. A model of mini-embolic stroke offers measurements of the neurovascular unit response in the living mouse. Stroke 2005; 36:2701-4.
49. Houng A K, McNamee R A, Kerner A, et al. Atrial natriuretic peptide increases inflammation, infarct size, and mortality after experimental coronary occlusion. American journal of physiology 2009; 296:H655-61.
50. Swanson R A, Morton M T, Tsao-Wu G, Savalos R A, Davidson C, Sharp F R. A semiautomated method for measuring brain infarct volume. J Cereb Blood Flow Metab 1990; 10:290-3.
51. Robinson B R, Houng A K, Reed G L. Catalytic life of activated factor XIII in thrombi. Implications for fibrinolytic resistance and thrombus aging. Circulation 2000; 102:1151-7.
52. Sazonova I Y, McNamee R A, Houng A K, King S M, Hedstrom L, Reed G L. Reprogrammed streptokinases develop fibrin-targeting and dissolve blood clots with more potency than tissue plasminogen activator. J Thromb Haemost 2009; 7:1321-8.
53. Zunker P, Schick A, Padro T, Kienast J, Phillips A, Ringelstein E B. Tissue plasminogen activator and plasminogen activator inhibitor in patients with acute ischemic stroke: relation to stroke etiology. Neurological research 1999; 21:727-32.
54. Wang X, Lee S R, Arai K, et al. Lipoprotein receptor-mediated induction of matrix metalloproteinase by tissue plasminogen activator. Nat Med 2003; 9:1313-7.
55. Hunter A J, Hatcher J, Virley D, et al. Functional assessments in mice and rats after focal stroke. Neuropharmacology 2000; 39:806-16.
56. Heinsius T, Bogousslaysky J, Van Melle G. Large infarcts in the middle cerebral artery territory. Etiology and outcome patterns. Neurology 1998; 50:341-50.
57. Yepes M, Sandkvist M, Moore E G, Bugge T H, Strickland D K, Lawrence D A. Tissue-type plasminogen activator induces opening of the blood-brain barrier via the LDL receptor-related protein. J Clin Invest 2003; 112:1533-40.
58. Asahi M, Wang X, Mori T, et al. Effects of matrix metalloproteinase-9 gene knock-out on the proteolysis of blood-brain barrier and white matter components after cerebral ischemia. J Neurosci 2001; 21:7724-32.
59. Montaner J, Molina C A, Monasterio J, et al. Matrix metalloproteinase-9 pretreatment level predicts intracranial hemorrhagic complications after thrombolysis in human stroke. Circulation 2003; 107:598-603.
60. Wang X, Tsuji K, Lee S R, et al. Mechanisms of hemorrhagic transformation after tissue plasminogen activator reperfusion therapy for ischemic stroke. Stroke 2004; 35:2726-30.
61. Kaur J, Zhao Z, Klein G M, Lo E H, Buchan A M. The neurotoxicity of tissue plasminogen activator? J Cereb Blood Flow Metab 2004; 24:945-63.
62. Tabrizi P, Wang L, Seeds N, et al. Tissue plasminogen activator (tPA) deficiency exacerbates cerebrovascular fibrin deposition and brain injury in a murine stroke model: studies in tPA-deficient mice and wild-type mice on a matched genetic background. Arteriosclerosis, thrombosis, and vascular biology 1999; 19:2801-6.

The invention claimed is:

1. A method of inhibiting disability or death from endogenous or pharmacologic tissue plasminogen activator (TPA) toxicity due to ischemia from stroke in a patient in need thereof, the method comprising:
   determining that the patient has or is at risk for TPA toxicity due to prolonged ischemia of at least three hours; and
   administering, in response to the determining the patient has or is at risk for TPA toxicity due to prolonged ischemia of at least three hours, to the patient an effective amount of a composition comprising an anti-SerpinF2 antibody or fragment thereof that reduces SerpinF2 activity or concentration, wherein the composition does not include TPA, thereby inhibiting disability or death from TPA toxicity due to ischemia from stroke.

2. The method of claim 1, wherein the determining step further comprises determining that the patient has neurologic symptoms indicative of neuronal damage.

3. The method of claim 1, wherein TPA has been previously administered to the patient within 48 hours.

4. The method of claim 1, wherein the anti-SerpinF2 antibody or fragment thereof is administered in a dose range from 28-91 nanomoles/kg.

5. A method of inhibiting disability or death from endogenous or pharmacologic tissue plasminogen activator (TPA) mediated neurologic hemorrhage or edema in a patient in need thereof, the method comprising:
   determining that the patient has or is at risk for TPA toxicity due to prolonged ischemia of at least three hours; and administering, in response to the determining the patient has or is at risk for TPA toxicity due to prolonged ischemia of at least three hours, to the patient an effective amount of a composition comprising an anti-SerpinF2 antibody or fragment thereof that reduces SerpinF2 activity or concentration, wherein the composition does not include TPA, thereby inhibiting disability or death from TPA mediated neurologic hemorrhage or edema.

6. The method of claim 5, wherein the determining step further comprises determining that the patient has neurologic symptoms indicative of neuronal damage.

7. The method of claim 5, wherein TPA has been previously administered to the patient within 48 hours.

8. The method of claim 5, wherein the anti-SerpinF2 antibody or fragment thereof is administered in a dose range from 28-91 nanomoles/kg.

9. A method of treating stroke in a patient affected by TPA toxicity, the method comprising:
    determining that the patient has or is at risk for TPA toxicity due to prolonged ischemia of at least three hours; and
    administering, in response to the determining the patient has or is at risk for TPA toxicity due to prolonged ischemia of at least three hours, to the patient an effective amount of a composition comprising an anti-SerpinF2 antibody or fragment thereof that reduces SerpinF2 activity or concentration, wherein the composition does not include TPA, thereby treating stroke in the patient affected by TPA toxicity.

10. The method of claim 9, wherein TPA has been previously administered to the patient within 48 hours.

11. The method of claim 9, wherein the anti-SerpinF2 antibody or fragment thereof is administered in a dose range from 28-91 nanomoles/kg.

12. The method of claim 1, wherein the TPA toxicity is determined by determining that the patient has neurologic symptoms.

13. The method of claim 5, wherein the TPA toxicity is determined by determining that the patient has neurologic symptoms.

14. The method of claim 9, wherein the TPA toxicity is determined by determining that the patient has neurologic symptoms.

15. The method of claim 1, wherein the anti-SerpinF2 antibody or fragment thereof is administered in a dose range from 17-50 nanomoles/kg.

16. The method of claim 5, wherein the anti-SerpinF2 antibody or fragment thereof is administered in a dose range from 17-50 nanomoles/kg.

17. The method of claim 9, wherein the anti-SerpinF2 antibody or fragment thereof is administered in a dose range from 17-50 nanomoles/kg.

* * * * *

UNITED STATES PATENT AND TRADEMARK OFFICE
CERTIFICATE OF CORRECTION

| | | |
|---|---|---|
| PATENT NO. | : 11,236,176 B2 | Page 1 of 1 |
| APPLICATION NO. | : 14/198804 | |
| DATED | : February 1, 2022 | |
| INVENTOR(S) | : Guy L. Reed | |

It is certified that error appears in the above-identified patent and that said Letters Patent is hereby corrected as shown below:

In the Specification

Column 1, Lines 16-19, please replace the paragraph under the ACKNOWLEDGEMENT OF FEDERAL RESEARCH SUPPORT from "This invention was made, in past, with Government support under National Institute of Health Grant Nos. HL092750 & NS073147. Accordingly, the United States Government has certain rights in this invention." to --This invention was made with government support under grants HL092750 and NS073147 awarded by the National Institutes of Health. The United States Government has certain rights in the invention.--

Signed and Sealed this
Thirty-first Day of December, 2024

Derrick Brent
*Acting Director of the United States Patent and Trademark Office*